United States Patent [19]

Shindo et al.

[11] Patent Number: 5,470,533
[45] Date of Patent: Nov. 28, 1995

[54] TEST STRIP SUPPLY APPARATUS AND ANALYZER USING SAME

[76] Inventors: Isao Shindo, 2714, Tsuda, Katsuta-shi, Ibaraki-ken; Shigeo Mutou, 982, Ochiaicho, Hitachiohta-shi, Ibaraki-ken; Takao Terayama, 56-100, Sakaecho 1-chome, Ushiku-shi, Ibaraki-ken; Masao Okayama, 7-8, Nagayama 1-chome, Ryugasaki-shi, Ibaraki-ken; Susumu Kai, Hitachi-wing 407, 11-1, Aobacho, Katsuta-shi, Ibaraki-ken, all of Japan

[21] Appl. No.: 149,084

[22] Filed: Nov. 9, 1993

[30] Foreign Application Priority Data

Nov. 11, 1992 [JP] Japan .................................. 4-300791

[51] Int. Cl.⁶ ........................... G01N 35/00; G01N 35/10
[52] U.S. Cl. ............... 422/63; 422/66; 422/68.1; 436/44; 436/46; 436/48
[58] Field of Search ................... 422/62, 63, 66, 422/68.1; 436/44, 46, 48, 171

[56] References Cited

U.S. PATENT DOCUMENTS

| | | | |
|---|---|---|---|
| 4,710,352 | 12/1987 | Slater et al. | 422/63 |
| 4,820,491 | 4/1989 | Khoja et al. | 422/63 |
| 4,876,204 | 10/1989 | Inoue et al. | 436/46 |
| 4,937,050 | 6/1990 | Meinecke et al. | 422/68.1 |
| 5,055,261 | 10/1991 | Khoja et al. | 422/64 |
| 5,143,694 | 9/1992 | Schafer et al. | 422/65 |
| 5,298,425 | 3/1994 | Kuhn et al. | 436/43 |

*Primary Examiner*—Robert J. Warden
*Assistant Examiner*—N. Bhat

[57] ABSTRACT

A test strip supply apparatus comprises a cylindrical container having an elongate test strip fitting penetration slot formed in its side wall, a container support having a semi-cylindrical concave surface formed in its upper portion and a test strip take-out hole formed at the center of the concave surface for allowing a test strip dropped from the penetration slot of the container to pass therethrough, and a test strip transfer stage for receiving the test strip dropped from the penetration slot and transferring it. A test strip reversing function is also provided such that during the transfer of the test strip by the transfer stage, optical means determines whether the test strip is placed facing properly or not and, if the back surface is on the upper side, the test strip is reversed upside down before further transfer.

10 Claims, 7 Drawing Sheets

TEST STRIP SUPPLY APPARATUS AND ANALYZER USING SAME

BACKGROUND OF THE INVENTION

The present invention relates to a test strip supply apparatus and an analyzer using the same, and more particularly to a test strip supply apparatus and analyzer which are effective in analyzing samples from the living body, such as urine and blood, by using test strips each having reaction layers impregnated with reagents.

Test strips are often used in medical examination in hospitals so that urine or blood samples can be simply examined for a plurality of analytical items. Each test strip comprises an elongate sheet-like strip made of plastic or the like onto which a plurality of reaction layers impregnated with reagents are clung.

One example of known automatic analyzers using such test strips is disclosed in JP, A, 61-91571. In this prior art, an arm having a test strip gripper is moved between a test strip supply mechanism, a sample table including sample containers which are placed on the table and in which test strips are to be dipped, and a photometric mechanism, thereby performing photomerry on each test strip which has developed colors in the reaction layers. The test strip supply mechanism supplies the test strips one by one to a position where the arm starts carrying the test strip. The test strip supply mechanism disclosed in JP, A, 61-91571 includes a hopper provided with the bottom movable transversely and each test strip is sent out of the hopper when the bottom is moved with respect to a hopper body in which the test strips are put beforehand.

SUMMARY OF THE INVENTION

A test strip is usually curved such that its surface onto which a plurality of reaction layers impregnated with reagents are clung becomes convex. An extent of the curvature is not constant and different from strip to strip, which has hindered automation of test strip supply apparatus. On the other hand, the test strip supply mechanism disclosed in the above-cited JP, A, 61-91571 has a problem that because the mechanism is arranged to take out a test strip just by sliding the bottom of the hopper, the test strip is likely to be caught between the bottom and wall of the hopper, making it hard to take out the test strip. Thus, due considerations for smoothly taking out curved test strips are not paid in the above prior art.

An object of the present invention is to provide a test strip supply apparatus and analyzer in which an operation of supplying test strips is failed at a less rate.

Another object of the present invention is to provide a test strip supply apparatus and analyzer by which even curved test strips can be smoothly and automatically supplied.

To achieve the above objects, the present invention is arranged such that test strips each having reaction layers impregnated with reagents are put in a container being preferably cylindrical in shape, and are successively delivered one by one out of the container through a penetration slot formed in the container. The container is provided therein with a guide member for guiding the test strip toward the penetration slot. The guide member includes an extended portion extending along an inner wall of the container. The container is associated with a test strip pushing device having a contact portion which can come into contact with the test strips. With relative movement between the container and the pushing device, the pushing device pushes the test strip into the guide member for smoothly introducing the test strip toward the penetration slot.

In a preferable embodiment of the present invention, at least one of both side ends of the guide member at its inlet is formed to have a height larger than that of a central portion of the guide member at its inlet. Here, the term "height" corresponds to the spacing distance between the inner wall of the container and the extended portion. Also, in a preferable embodiment, the pushing device is arranged such that its contact portion is moved back outwardly of the container when an excessive force is applied to the contact portion. The relative movement between the pushing device and the container for pushing the test strip into the guide member can be effected by, for example, moving the pushing device while keeping the container stationary, or moving or rotating the container while keeping the pushing device substantially stationary, or moving both the container and the pushing device.

In a preferable embodiment of the present invention, the relative movement between the container and the pushing device is effected by adopting the method of moving the container while keeping the pushing device substantially stationary. Therefore, the following description will be described primarily in connection with that method.

When the movable container containing a plurality of test strips is reciprocally rotated, the test strips are moved in a direction almost perpendicular to the direction of their length with rotation of the container wall. The distance over which the container is reciprocally rotated (i.e., the angular range of the rotation) is set to a predetermined value. The container is reciprocally rotated in such opposite directions that the guide member moves toward and away from the test strip contact portion of the pushing device. When the guide member moves toward the test strip contact portion of the pushing device, one or more test strips locating near the inlet of the guide member are kept from moving in the container by the test strip contact portion. Then, as the guide member further approaches the contact portion, those test strips are pushed into the guide member. Accordingly, even when the test strips are gently curved and likely undergo resistance at the time of entering the guide member, they can be somewhat forcibly pushed to slide into the penetration slot formed in the container wall.

In a preferable embodiment of the present invention, the pushing device comprises a fixed portion fixed outside the container, the test strip contact portion arranged to be able enter an inner space of the container, and an acting force responsive member (e.g., a leaf spring) for integrally connecting the fixed portion and the test strip contact portion to each other. As occurred in such a case that at the time an innermost wall surface of the guide member locating at its inner bottom maximally approaches the test strip contact portion of the pushing device, there are present two or more test strips adjacent each other between the test strip contact portion and the innermost wall surface of the guide member, when an excessive force is applied to the test strip contact portion, the test strip contact portion is moved back outwardly of the container with the aid of the acting force responsive member, thereby protecting the test strips from damage. The container is reciprocally rotated by a drive device with a predetermined amplitude or angular range so that the maximally approached distance between the test strip contact portion and the innermost wall surface of the guide member is almost equal to the width of the test strip.

While a preferable embodiment of the present invention will be explained below as using one set of the guide member and the test strip pushing device, the set of both the components may be provided in plural number to more efficiently supply the test strips out of the container. Further, in a preferable embodiment of the present invention, in order to that the guide member can accommodate even those test strips which are curved to a greater extent than usual, the guide member is formed to such a inlet configuration as to provide a larger gap at its both side ends than that at its central portion with respect to the inner wall of the container.

DETAILED DESCRIPTION OF THE PREFERRED EMBODIMENTS

Figure 1:
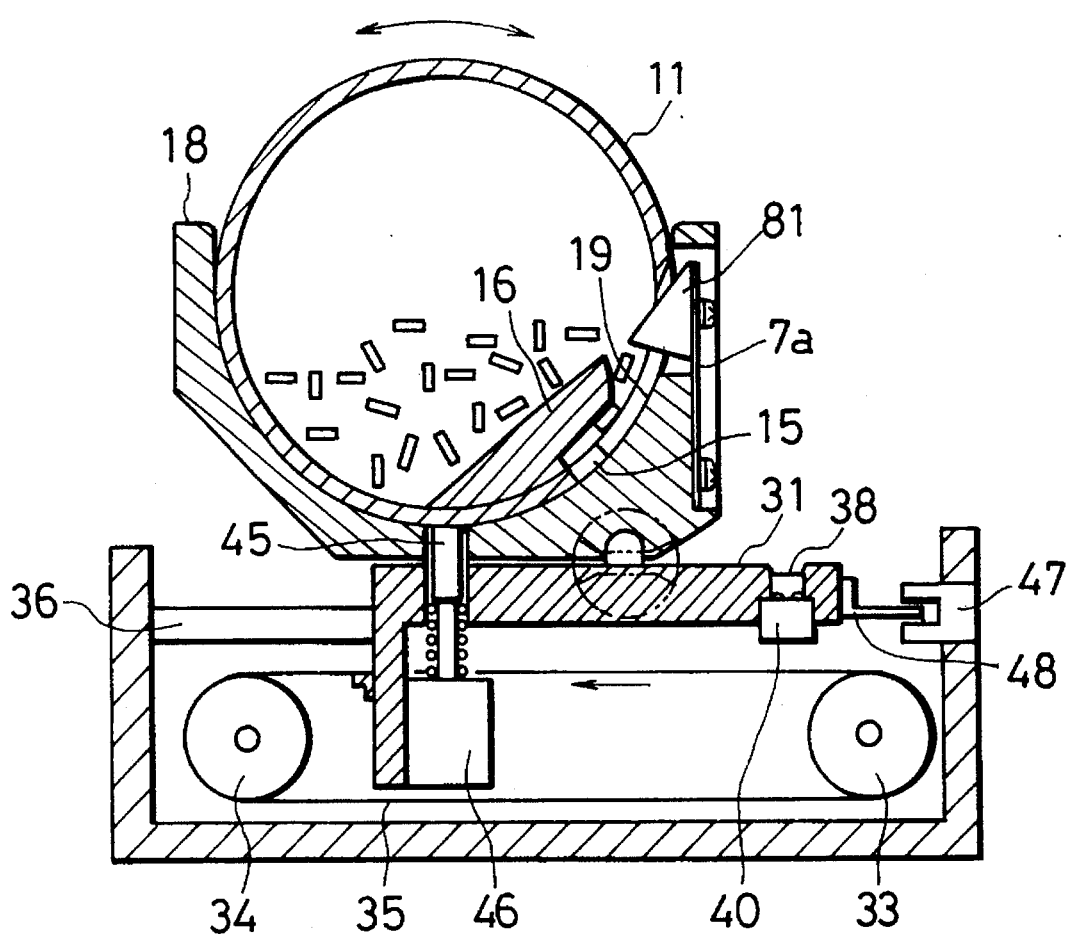
FIG. 1 is a vertical sectional view of principal parts of a test strip supply apparatus for use with an analyzer of FIG. 7 to which the present invention is applied.
Figure 2:
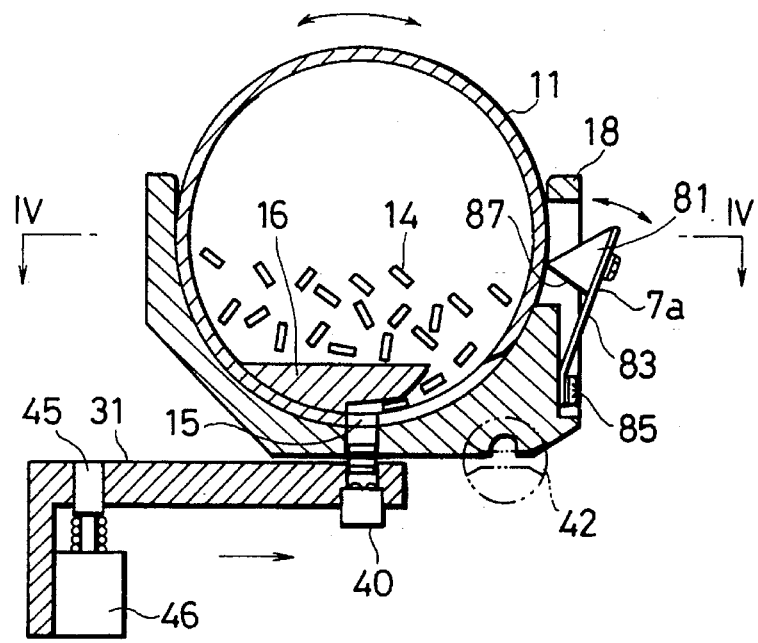
FIG. 2 is a similar sectional view for explaining the operation of the apparatus of FIG. 1.

An embodiment to which the present invention is applied will be hereinafter described with reference to FIGS. 1 to 11. FIG. 7 is a view schematically showing the entire arrangement of an analyzer adapted to analyze samples from the living body, such as urine and blood, by using test strips. The analyzer comprises a sample positioning apparatus 51, a test strip automatic supply apparatus 52, a test strip holding/carrying apparatus 53 for gripping and carrying test strips one by one, a photometric apparatus 54 including a photometer 63, and a processing unit 55 for processing measured data and controlling operations of respective mechanisms in the analyzer. The arrangements and functions of those components will be described later.

Figure 8:
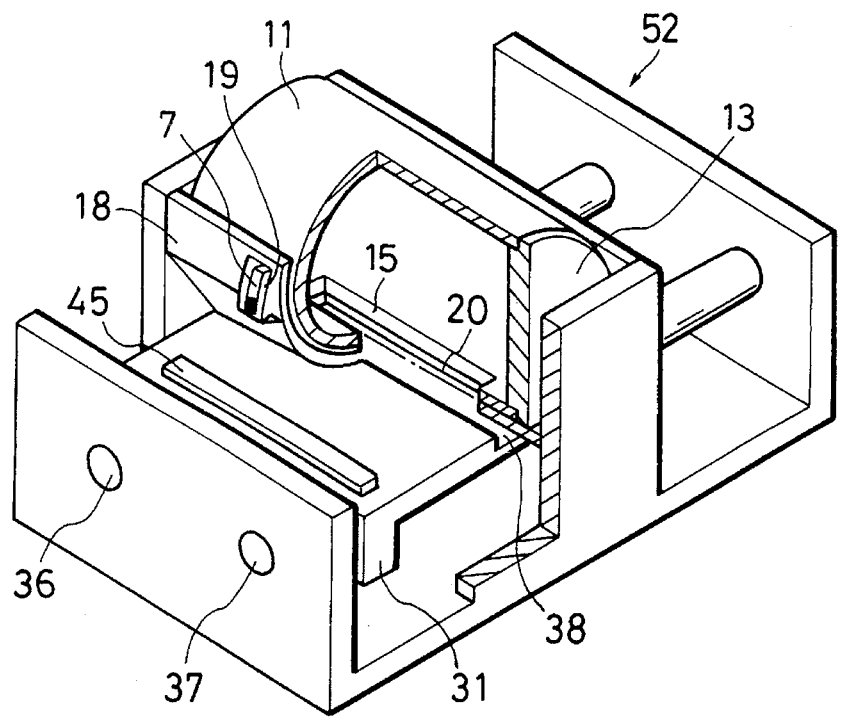
FIG. 8 is an appearance view, partly broken away, of the apparatus of FIG. 1.

FIG. 8 is a perspective view, partly broken away, showing an appearance of the test strip automatic supply apparatus 52. A test strip container 11 has a lid 13 detachably attached to its open end, and a number of elongate test strips are put in the test strip container 11 so as to lie in the longitudinal direction of the container 11. The test strip container 11 is accommodated in a support 18 of which inner surface is formed to curve following an outer surface of the container 11, but it can be removed out of the support on occasion so that the lid 13 is optionally opened and closed.

Although a guide member is disposed inside the container 11, FIG. 8 shows a condition except the guide member for convenience of description. The container 11 is swung by a drive device (described later) in the clockwise or counterclockwise direction over an angular range of 90 degrees, but it is stopped at the time the test strip is delivered out of the container 11. In this stopped state, a penetration slot 15 formed through a wall of the container 11 is positioned just below the center of rotation of the container 11. The position of the penetration slot 15 is thereby made coincident with the position of a communication hole 20 formed in the support 18. This enables one of the test strips in the container 11 to pass through the penetration slot 15 and the communication hole 20 and then to be placed in an elongate test strip receiving groove 38 formed in a horizontally movable stage 31. After that, upon the stage 31 being slid to the right in FIG. 8, the test strip in the receiving groove 38 comes to a pickup position open to the outside.

During the time in which the container 11 is swung or rotated reciprocally, a belt-shaped shutter 45 is fitted into the communication hole 20 of the support 18 to prevent the test strip from entering the hole 20. A test strip containing chamber defined inside the container 11 has a length slightly greater than that of the test strips. The penetration slot 15 and the communication hole 20 are formed to be elongate in conformity with the shape of the test strips, and are dimensioned to allow the test strips to pass therethrough with no resistance. A pair of slots 19 are cut through the curved wall of the container 11, and test strip contact portions of a pushing device 7 can pass through the slots 19 to extend into an inner space of the container 11. The stage 31 can slide horizontally while being guided by a pair of guide shafts 36, 37.

Figure 6A:
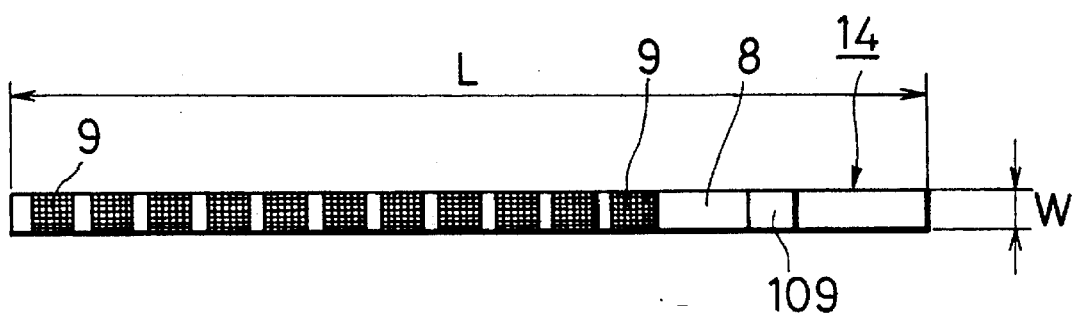
FIGS. 6A, 6B and 6C are views showing an example of a test strip.
Figure 6B:
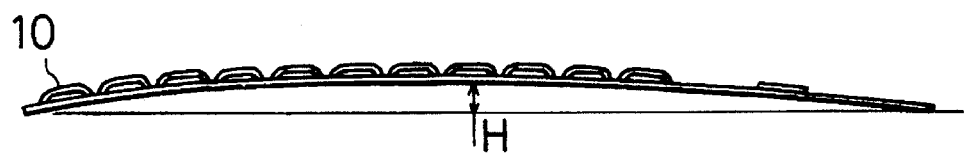
Figure 6C:
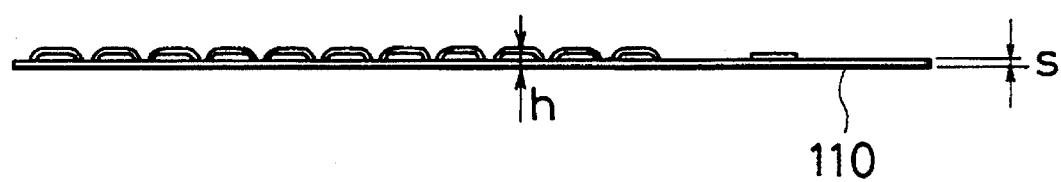
Figure 7:
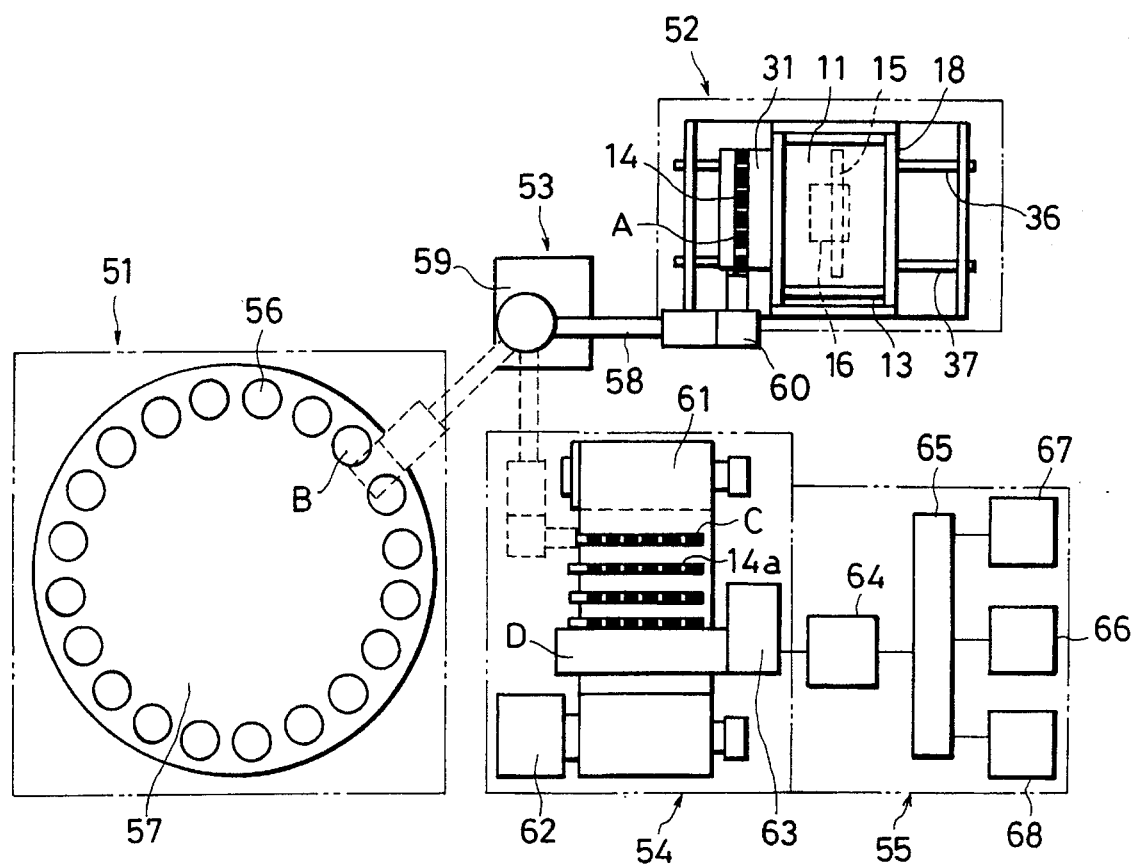
FIG. 7 is a view schematically showing the entire arrangement of an analyzer to which the present invention is applied.

An example of the test strips put in the container 11 is shown in FIGS. 6A, 6B and 6C. A test strip 14 comprises an elongate sheet-like stick 8 made of plastic and having a length of L, and a plurality of, e.g., eleven, reaction layers 9 impregnated with reagents which layers are covered by thin mesh-like cloth 10 for clinging to one surface of the stick 9. After all those eleven reaction layers 9 have been simultaneously dipped in a sample, the test strip is lifted out of the sample, causing coloration to develop in the reaction layers. Generally, the reaction layers 9 are each about 5 mm×5 mm in square and 0.5 to 1.5 mm thick. The test strip 14 shown in FIGS. 6A, 6B and 6C, by way of example, has a length L of 120 mm, a width w of 5 mm and a height h of 1.8 mm. When the test strip 14 is dipped in a sample, the mesh-like cloth 10 covering the reaction layers to fix them acts to make the test strip 14 concaved on the reaction layer side because of its shrinkage. Therefore, the test strip 14 is curved with a maximum elevation H of 1 to 4 mm in advance so that the test strip changes from a curved shape of FIG. 6B into a flat shape of FIG. 6C when it absorbs the sample. The reaction layers 9 are formed of filter paper or felt. The test strip 14 also includes a reference surface 109 and a grip region 110.

Of the analyzer, shown in FIG. 7, handling the test strips for measurement, the sample positioning apparatus 51 shifts sample containers 56, which are arrayed on a turntable 57 and contain urine samples, to a test strip dipping position B successively. On the other hand, the test strip automatic supply apparatus 52 supplies the test strips 14 from the cylindrical container 11, which contains a number of test strips, to a predetermined external take-out position (pickup position) A one by one. Supply of the test strip to the external take-out position A is performed in synchronism with an operation cycle of the analyzer. The lid 13 is attached to the cylindrical container 11 at its end face corresponding to the upper or lower bottom, allowing the test strips to be put into or removed out of the container 11. The penetration slot 15 is formed through the curved wall of the cylindrical container 11 to position at the lowest level in its rest state, and a guide member 16 is disposed to cover the penetration slot 15 in spaced relation so that the test strip is guided to be surely fitted into the penetration slot 15. The cylindrical container 11 is slidably placed on the container support 18 which also serves as a test strip escape preventing member and an open air shielding member. As also shown in FIG. 1, the container support 18 is provided with the test strip pushing resilient member 7a for introducing the test strip 14 into the guide member 16. With the cylindrical container 11 swung or rotated reciprocally over a predetermine angle, the test strip 14 is pushed to come into the guide member 16 and then enter the penetration groove 15. The rotation of the cylindrical container 11 is stopped at the time the penetration groove 15 is positioned at the lowest level, following which the shutter 45 is descended. The test strip transfer stage 31 for moving the test strip fallen from the penetration slot 15 to the external take-out position A is installed below the support stand 18 and movable on the pair of guide shaft 36, 37 (see FIG. 4) such that an upper surface of the transfer stage 31 is kept in slide contact with a lower surface of the support 18 during the movement.

The test strip holding/carrying apparatus 53 shown in FIG. 7 comprises an arm 58 capable of turning about its base end, a drive mechanism 59, and a test strip gripper 60 attached to near a distal end of the arm 58. The holding/carrying apparatus 53 grips the test strip 14 supplied to the external take-out position A by the gripper 60, carries it to the dipping position B, and then dips all the reaction layers 9 of the test strip 14 into a sample in the sample container 56 at the dipping position B while gripping it. After being dipped for a predetermined period of time, the test strip 14 is lifted out of the sample, carried to the photometric apparatus 54, and then released from the gripper 56 at a test strip set position C. Thereafter, the gripper 60 returns to the external take-out position A in the test strip supply apparatus 52. Until this time, the next test strip has been supplied to the external take-out position A. The process will be repeated during the analyzing operation.

In the photometric apparatus 54, rolled paper 61 is used to transport a test strip 14a received from the test strip holding/carrying apparatus 53 and being under color reactions. The rolled paper 61 is intermittently let out and wound by a reeling mechanism 62 with predetermined time intervals so that the test strip 14a put in the set position C is transported to a photometric position D. After the elapse of a predetermined time from the dipping into the sample, the test strip 14a is positioned at the photometric position D where photomerry is performed by the photometer 63. The photometer 63 includes a plurality of small-sized reflection type detectors comprising pairs of light sources for emitting lights of particular wavelengths corresponding to respective analysis items and light receiving elements formed of silicon photo diodes. Those detectors are arrayed corresponding to respective positions where the reaction layers of the test strip 14a are to be measured, thereby measuring the intensity of lights reflected from the reaction layers on which the colors specific to the reactions are developing. The measured results are transmitted to a control unit 65 via an A/D converter 64 for data processing to be indicated on a liquid crystal display 66 and also printed out by a printer 67. The analyzing operation in the present analyzer is progressed in accordance with inputs entered from a control panel 68. The test strip completely measured is wound up along with the paper by the reeling mechanism 62 into a roll. After completion of the measurement, therefore, the test strips can be removed and discarded together with the rolled paper.

Figure 3:
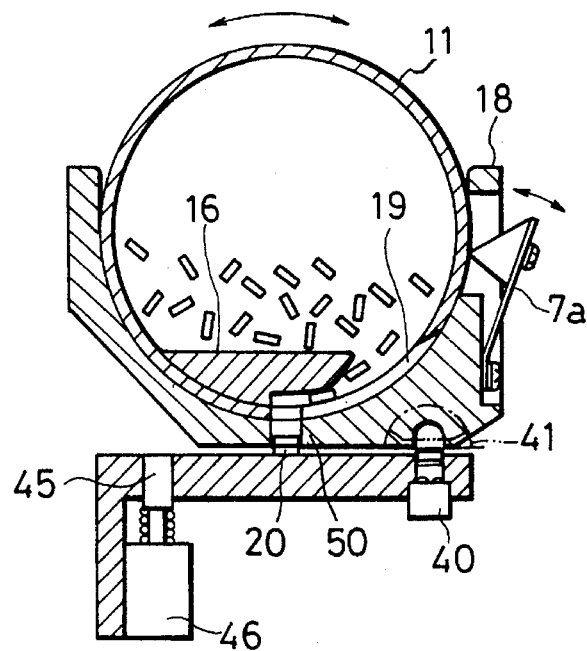
FIG. 3 is a similar sectional view for explaining the operation of the apparatus of FIG. 1.
Figure 4:
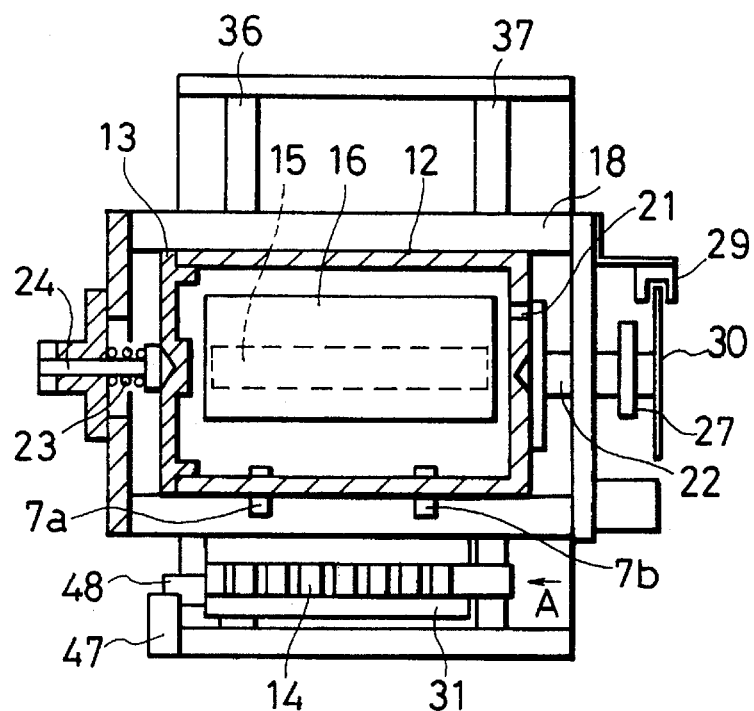
FIG. 4 is a sectional view taken along line IV—IV in FIG. 2.

The detailed construction of the test strip automatic supply apparatus 52 adopted in the analyzer of FIG. 7 will now be described with reference to FIGS. 1 to 5 and FIGS. 8 to 11. While it is conceivable to form the container 11 for containing a number of test strips in various shapes such as a polygonal tube, a cylindrical container is shown, by way of example, in those figures. The cylindrical container 11 comprises a container body 12 and the lid 13, as shown in FIG. 4. A space in the container body 12 between the bottom and the lid 13 defines the test strip containing chamber, and the distance between the container bottom and the lid 13, i.e., the depth of the test strip containing chamber, is set slightly greater than the length L of the test strip 14. With such an arrangement, when the cylindrical container 11 is rotated reciprocally after putting the test strips in the container to lie in the longitudinal direction, those test strips will not direct in different ways.

Figure 9:
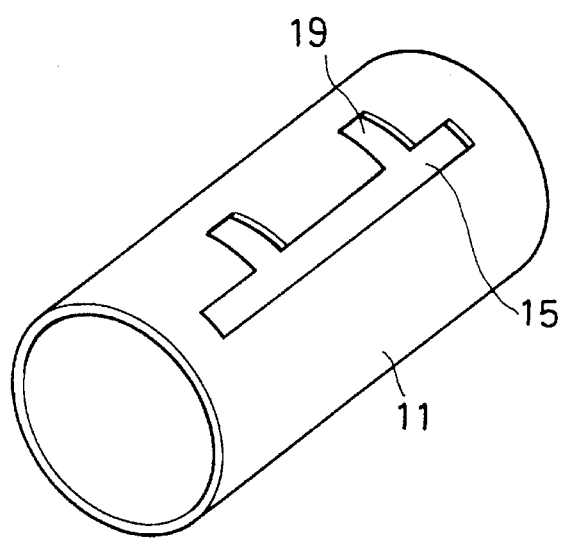
FIG. 9 is an appearance view of a cylindrical container used in the apparatus of FIG. 1.

In the curved wall of the cylindrical container 11, there are formed the rectangular penetration slot 15 which is extended parallel to the axis of rotation of the container 11 and which is sized and shaped so as to allow the test strip 14 to be fit into and pass through the slot 15, and the pair of slots 19 through which test strip pushing resilient members 7a, 7b can pass (see FIG. 9). The penetration slot 15 is slightly longer than the length L of the test strip 14 and slightly wider than the width w of the test strip 14. Also, the depth of the penetration slot 15 (the thickness of the wall in the illustrated example) is almost equal to the height h of the test strip 14. Disposed parallel to the penetration slot 15 is the guide member 16 on the same side as the axis of rotation of the container 11. More specifically, the guide member 16 has a base portion 75 (see FIG. 10) fixed to an inner wall surface of the container 11 such that, for example, the test strip which is going to enter from the counterclockwise side is introduced to the penetration slot 15, but the test strip which is going to enter from the clockwise side is blocked from entering the penetration slot 15. The test strip 14 is usually curved with a maximum elevation of 1 to 4 mm, as shown in FIG. 6B.

Figure 10:
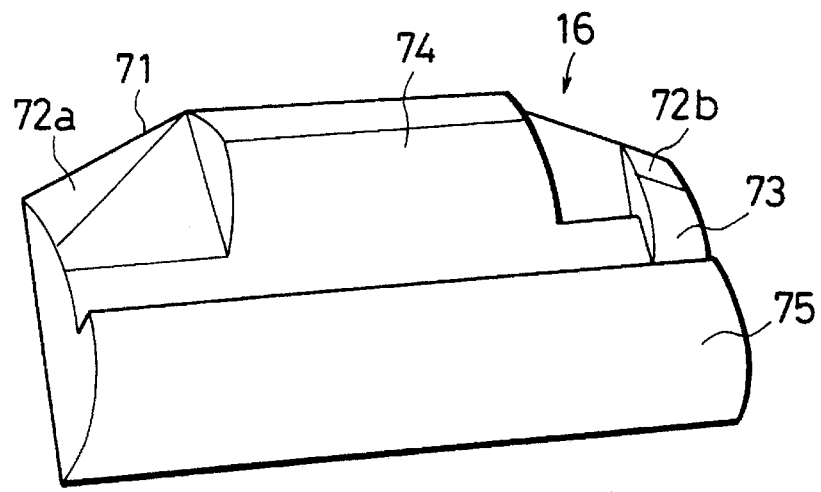
FIG. 10 is a perspective view when a guide member is viewed from below.
Figure 11:
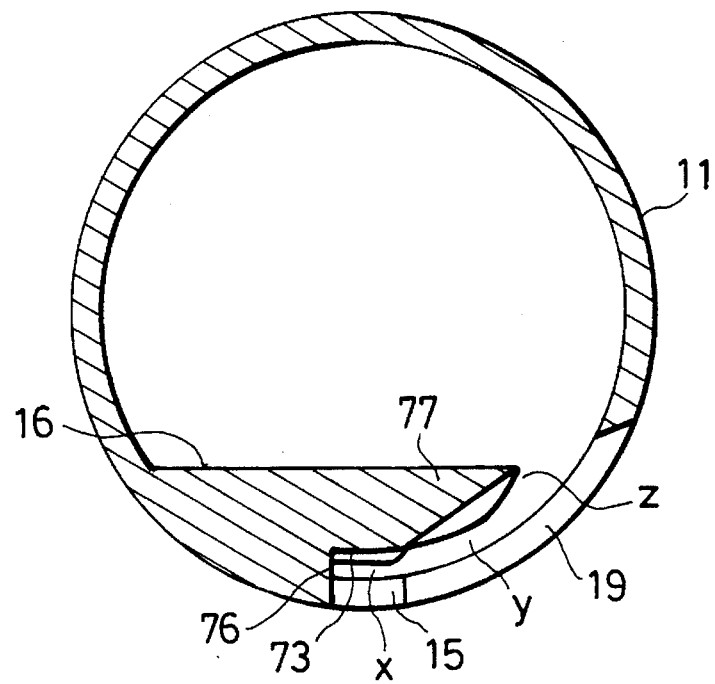
FIG. 11 is a cross-sectional view of the cylindrical container.

A description will now be given of the guide member 16 disposed in the container 11 with reference to, especially, FIGS. 10 and 11. The guide member 16 comprises an extended portion 77 extending substantially along the inner wall of the container 11 and having a bottom surface 76 at its innermost end, and the base portion 75 integrally joined to the inner wall of the container 11. The extended portion 77 covers in spaced relation the penetration slot 15 formed in the wall of the container 11. The surface of the guide member 16 facing the penetration slot 15 has a rather complicated configuration as seen from FIG. 10. More specifically, that surface includes a projected region 74 almost centrally positioned in the longitudinal direction of the container 11, surfaces defining both inlet ends 72a, 72b, and a step defining surface 73 provided only on the side of one inlet end. The spacing distance y between the surface of the projected region 74 and the inner wall surface of the container 11 is larger than the thickness h of the test strip 14, but smaller than $2h$, i.e., twice the thickness h thereof. The area near the inlet end 72a is cut out or chamfered so as to present the spacing distance larger than the maximum elevation H of the test strip 14 in its curvature. The spacing distance formed until reaching the penetration slot 15 between the guide member 16 and the inner wall of the container 11 is equal to the thickness h of the test strip 14 even at the narrowest portion. The pair of elongate slots 19 are defined through the wall of the container 11 to extend in a direction perpendicular to the longitudinal direction of the container, i.e., in the direction of reciprocal rotation of the container.

Further, in order to make the test strip easily enter the gap between the guide member 16 and the inner wall of the container 11, the guide member 16 is rounded at its distal end 71. The gap size Z at the inlet of the guide member 16 is in the range of 0.5 to 1.0 time the width W of the test strip 14 so that the test strip 14 can easily enter the gap beneath the guide member 16. The spacing distance between the extended portion of the guide member 16 and an upper edge of the penetration slot 15 is, on the side of the inlet end 72a, larger than the thickness h of one test strip 14, but smaller than 2h, i.e., twice the thickness h thereof. On the side of the inlet end 72b, however, that spacing distance has a size x slightly smaller than the thickness h of one test strip 14 by the presence of the step defining surface 73. With such an arrangement, the two test strips 14 are prevented from obliquely overlapping at their portions inclusive of no reaction layers 9 in the penetration slot 15, whereby the test strips 14 can be smoothly introduced to the penetration slot 15 one by one.

Figure 5:
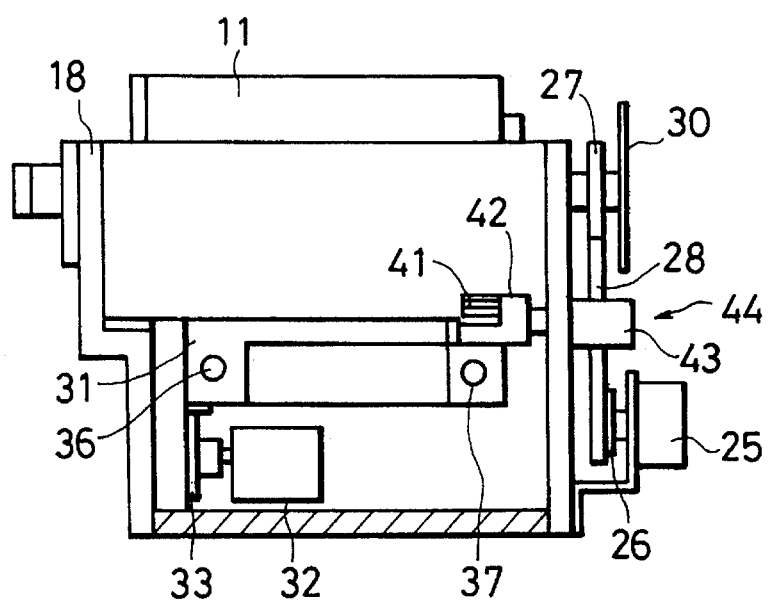
FIG. 5 is a front appearance view of the apparatus of FIG. 1.

The cylindrical container 11 is rotated reciprocally by a pulse motor 25 as a rotation driving source, shown in FIG. 5. When the container 11 is rotated counterclockwise as shown in FIG. 1, the test strip 14 is introduced by forces imposed from the test strip pushing resilient members 7a, 7b to enter the penetration slot 15 with the aid of the guide member 16. Since the pushing resilient members 7a, 7b act to return the second and subsequent test strips toward the inlet side of the guide member 16 when the container 11 is rotated clockwise, the first or leading test strip will not be prevented from falling down onto the transfer stage 31 by being pressed by the second or succeeding one.

The angular range of reciprocal rotation of the container 11 (about its own axis) is controlled by the control unit 65 based on a signal provided by, as shown in FIG. 4, a combination of a notched disk 30 mounted to a rotary shaft 22 of a torque transmitting mechanism and a notch position sensor 29 attached to the support 18 which is stationarily installed. The angular range of reciprocal rotation of the cylindrical container 11 about its own axis is about 85 degrees in the clockwise direction and about 78 degrees in the counterclockwise direction from the stopped position in this embodiment.

The bottom side of the container 11 is held in engagement with a torque transmitting boss 21 (see FIG. 4) of the torque transmitting mechanism, while the lid 13 of the container 11 is supported by a support shaft 24 provided with a pressing spring 23. By pushing the container body 12 to the left in FIG. 4, therefore, the container body 12 is disengaged from the projection 21 and the container can be removed upwards. Although the only one penetration slot 15 is formed in the container 11 in the illustrated embodiment, the penetration slot may be formed two or more depending on cases.

The longitudinal outer surface of the cylindrical container 11 is formed to be slidable with respect to the curved inner surface of the container support 18. The container support 18 also serves to prevent the penetration slot 15 from being open to the outside during the rotation of the container 11. If the penetration slot 15 is open to the outside, the test strips would be escaped out of the container 11 through the penetration slot 15. For this reason, the support 18 is arranged to entirely cover the region over which the penetration slot 15 is angularly moved during the rotation of the container 11, so that it can serve as a member for preventing escape of the test strips. Also, because the reaction layers 9 of the test strips put in the container 11 usually tend to degenerate during a long period of time due to moisture, the inner space of the container 11 is maintained at low humidity by a desiccant. Thus, another reason why the support 18 is arranged to cover the outer circumference of the container 11 over the entire region of movement of the penetration slot 15 is to prevent open air from entering the container 11 through the penetration slot 15 as far as possible.

The support 18 as the test strip escape preventing member covers the outer circumference of the container 11 at the bottom thereof as well, but it is required to take out the test strip from the bottom of the container 11. Therefore, the support 18 has the rectangular communication hole 20 formed at a predetermined position becoming coincident with the penetration slot 15 when the rotation of the container 11 is stopped, so that the test strip is allowed to pass from the penetration slot 15 toward the test strip transfer stage 31. The communication hole 20 is closed by the shutter 45 during the rotation of the container 11 and opened only when the test strip is to be dropped from the container. The dropped test strip is set in the test strip receiving groove 38 formed in the upper surface of the transfer stage 31 which can slide over the pair of guide shaft 36, 37. The length and width of the receiving groove 38 are formed to accommodate the size of the test strip.

One of side wall members disposed on both sides of a longitudinal member of the container support 18 defining its inner curved concave surface supports the torque transmitting mechanism. As shown in FIG. 3, the communication hole 20 is formed through the support 18 at the center of its inner concave semicylindrical surface. The cylindrical test strip container 11 is preferably made of light-transparent material such as acrylic resin. The support 18 in the illustrated embodiment supports the container 11 to be rotatable until 90 degrees in each of the clockwise and counterclockwise directions for the allowable angular range of the reciprocal rotation.

The cylindrical container 11 is supported by the rotary support shaft 22 having the boss 21 for torque transmission, and the movable support shaft 24 provided with the spring 23 for pressing the container 11 in the axial direction. The force for rotating the container 11 is transmitted from the pulse motor 25 through pulleys 26, 27 and a timing belt 28. The angle of rotation of the container 11 is detected by the sensor 29 and the rotary disk 30 having notches formed along its circumference, and controlled by the control unit 65.

The test strip transfer stage 31 is intermittently reciprocally moved along the pair of guide shafts 36, 37 in the horizontal direction by a motor 32 (FIG. 5), pulleys 33, 34 (FIG. 1) and a timing belt 35. The test strip receiving groove 38 formed in the upper surface of the transfer stage 31 receives the test strip dropped through the communication hole or test strip outlet hole 20 of the container support 18 and then transfers it to the external take-out position A. At the bottom of the test strip receiving groove 38, a front/back sensor 40 (FIG. 2) is provided for optically detecting whether the test strip is placed facing properly or not. A front/back reversing mechanism 44 comprising a rotating member 42 formed with a split groove 41 and a motor 43 (FIG. 5) for driving the rotating member 42 is provided to face a transfer passage of the transfer stage 31. When the test strip 14 is placed with its back side facing upwardly, the rotating member 42 is rotated 180 degrees at the time the grip of the test strip is positioned in the split groove 41, so that the test strip is reversed to direct properly. The shutter 45 (FIGS. 1 and 2) is provided to open and close the test strip outlet hole 20 of the container support 18 and is operated by a solenoid 46. A sensor 47 and an end lug 48 cooperating with the sensor 47, shown in FIG. 1, are provided to determine the stop position of the transfer stage 31.

In this embodiment, the number of test strips loadable into the cylindrical container 11 at a time is 200 and the test strips 14 are loaded in the container 11 such that their grip regions 110 extend toward the bottom of the container 11 (to the right in FIG. 4). The operation of the test strip supply apparatus is started in a condition that the container 11 is set in place and the hole 20 of the container support 18 is closed by the shutter 45.

The pushing resilient members 7a, 7b as the test strip pushing device each comprise a fixed portion 85 fixed to the container support 18, a contact portion 81 coming into contact with the test strips 14 in the container 11, and a leaf spring 83 interposed between the fixed portion 85 and the contact portion 81. In the case of using the test strip as shown in FIG. 6A, a care must be paid not to damage the test strip when it is inserted to the gap between the guide member and the inner wall of the container. To this end, the strength of the leaf spring 83 is set to 15 gf when the contact portion 81 is to be moved 2 mm forwards and backwards. If the spring strength is more than 50 gf, the test strip would be damaged and, therefore, the spring strength should be set less than 50 gf. However, if it is too weak, the pushing resilient members could not push the test strip into the gap beneath the guide member 16. Thus, the spring strength is required to be larger than the resisting forge (repellent forge) of the curved test strip.

The contact portions 81 can enter the inner space of the container 11 while passing through the corresponding slots 19, but the pushing device is installed such that the depth by which the contact portions 81 can enter will not exceed the height of the guide member 16 at its upper end. The shape of each contact portion 81 is preferably almost wedge-like in section. This wedge-like shape is effective in returning those test strips, which are not required to be pushed to the penetration slot 15, toward the inlet side of the guide member 16 when the contact portions 81 are moved back outwardly of the container 11.

The operation of the pulse motor 25 is controlled by the control unit for reciprocally rotating the cylindrical container 11 several times. With the reciprocal rotation of the container 11, the many test strips 14 put in the container 11 are moved correspondingly in a direction almost perpendicular to the direction of their own length. Since the penetration slot 15 of the container 11 rotates over about 85 degrees in the clockwise direction and about 78 degrees in the counterclockwise direction from the stopped position in FIGS. 1 to 3, the inner bottom surface 76 (see FIG. 11) of the guide member 16 maximally approaches pushing surfaces (see FIG. 2) of the contact portions 81 of the pushing device when the container 11 has rotated 78 degrees in the counterclockwise direction. The contact portions 81 are arranged such that, in the above maximally approached condition, the distance between the inner bottom surface 76 and the pushing surfaces 87 is almost equal to the width W of the test strip 14.

When an excessive force is applied to the test strip contact portions 81 of the pushing device, the contact portions 81 are moved back outwardly of the container 11. This outward movement is effected with resiliency of the leaf spring 83. Assuming now, for example, that two or more test strips are present near the inlet of the guide member 16 in the condition of FIG. 2, when the container 11 is rotated counterclockwise, the pushing surfaces 87 of the contact portions 81 keep those test strips from moving in the container 11 and hence the two or more strips are pushed side by side into the gap beneath the guide member 16. In this case, the two or more strips enter the gap beneath the guide member 16 with the relatively approaching movement of the container 11 and the contact portions 81, but only the leading test strip is introduced to the penetration slot 15. In the maximally approached condition, the pushing surfaces 87 approach the inner bottom surface 76 while leaving the distance of about W therebetween and, at this time, the presence of the second and succeeding test strips applies an excessive force to the contact portions 81. In such a case, the contact portions 81 are moved back while pressing the rear surfaces of the second and succeeding test strips at distal ends of their wedge-like shapes. As a result, the second and succeeding test strips are dragged to return toward the inlet side of the guide member 16 when the container 11 is rotated clockwise.

The operation procedures of the test strip supply apparatus of this embodiment will now be briefly described.

The pulse motor 25 is energized to reciprocally rotate the cylindrical container 11 several times so that one test strip is fitted in the penetration slot 15 with the aid of the test strip pushing device. In the illustrated embodiment, by reciprocally rotating the container 11 to the left and right three times, the test strip can be almost surely fitted in the penetration slot 15. Then, in a condition that the penetration slot 15 of the container 11 is made coincident with the hole 20 of the container support 18, the shutter 45 is descended to open the hole 20, causing the test strip to fall down on the transfer stage 31. At this time, the second test strip may also fall down in stacked relation succeeding to the first test strip to be taken out. After that, the transfer stage 31 is moved rearward (to the left in FIG. 1) to make the test strip receiving groove 38 positioned just below the hole 20 so that the fallen test strip is dropped and set in the groove 38 (see FIG. 2).

The transfer stage 31 is moved forwards (in the direction of arrow in FIG. 2) for transporting the test strip to the external take-out position A. At this time, the second test strip fallen down to overlie the first one is held in the hole 20 or at an outlet thereof by a block wall 50 (see FIG. 3) present downstream of the lower end of the hole 20 for preventing the movement of the second test strip. During the transport of the test strip, the front/back sensor 40 detects whether the test strip is placed facing properly or not. If the back surface of the test strip is on the upper side, the test strip is reversed upside down to face properly by the front/back reversing mechanism 44 (see FIG. 3). When the test strip reaches the external take-out position A, the shutter is restored to the position corresponding to the hole 20 and the solenoid 46 is energized to push up the remaining test strip for returning it into the container 11 while closing the hole 20. Following that, the operation of taking out the next test strip is started.

By repeating the above-explained operation, the test strips loaded in the cylindrical container 11 can be automatically and successively delivered to the test strip supply position. When the test strip supply apparatus of this embodiment is used with an automatic urine analyzer, the test strips can be supplied at a rate of one strip per 12 seconds.

According to the present invention, as described above, since a failure rate of the supply operation of test strips is remarkably reduced, automatic successive supply of the test strips can be smoothly progressed.

What is claimed is:

1. A test strip supply apparatus comprising a container for containing elongate test strips each having reaction layers impregnated with reagents, said container having a penetration slot through which said test strips are to be successively delivered out Of said container, a guide member including an extended portion which extends over said penetration slot of said container and guiding said test strip in said container toward said penetration slot, and a pushing device for pushing said test strip into said guide member with relative movement between said container and said pushing device; wherein said pushing device approaches the guide member in said container when said guide member moves in a first direction, and said pushing device goes away from said guide member when said guide member moves in a second direction opposite of said first direction.

2. A test strip supply apparatus according to claim 1, wherein said pushing device is movable back and forth to be moved outwardly of said container.

3. A test strip supply apparatus according to claim 1, wherein said pushing device includes a contact portion with said test strips and a fixed portion, said contact portion being able to enter an inner space of said container and said fixed portion being fixed outside said container.

4. A test strip supply apparatus according to claim 3, wherein said relative movement is effected in such a manner that said pushing device is held at a predetermined position and said container is reciprocally rotated.

5. A test strip supply apparatus according to claim 3, wherein said pushing device is arranged such that the depth by which said contact portion can enter the inner space of said container will not exceed the height of said guide member at its upper end.

6. A test strip supply apparatus according to claim 3, wherein said pushing device includes a plurality of said contact portions.

7. A test strip supply apparatus according to claim 1, wherein said guide member is formed to project in its lower central surface, and the gap between said projected surface and an inner wall of said container is in the range of 1 to 2 times the thickness of said test strips.

8. A test strip supply apparatus according to claim 7, wherein the inlet height of said guide member with respect to inner wall of said container is less than the width of said test strips.

9. A test strip supply apparatus comprising a movable container having a penetration slot through which each of test strips put in said container is to be successively delivered out of said container, a guide member formed in said movable container guiding said test strip in said container toward said penetration slot, at least one of both side ends of said guide member at its inlet having a height larger than the height of a central portion of said guide member at its inlet, a pushing device for pushing said test strip into said guide member with movement of said movable container, and a drive device for driving said movable container such that the maximally approached distance between an innermost wall surface of said guide member and a test strip contact surface of said pushing device is almost equal to the width of said test strips.

10. An analyzer comprising a container for containing a plurality of test strips each having reaction layers impregnated with reagents, said container having a penetration slot through which each of said test strips is to be successively delivered out of said container, a guide member including an extended portion which extends along an inner wall of said container and guiding said test strip in said container toward said penetration slot, a pushing device for pushing said test strip into said guide member with relative movement between said container and said pushing device, wherein said pushing device approaches the guide member in said container when said guide member moves in a first direction, and said pushing device goes away from said guide member when said guide member moves in a second direction opposite of said first direction, a transfer device for transferring said test strip delivered through said penetration slot in said test container to a take-out position, and a carrying device for gripping said test strip at said take-out position, dipping said test strip into a sample liquid while gripping said test strip, and then setting said test strip lifted out of said sample liquid into a photometric device.

* * * * *